United States Patent
Syudo

(10) Patent No.: US 6,528,077 B1
(45) Date of Patent: Mar. 4, 2003

(54) CATAPLASMS CONTAINING VITAMIN C OR ITS DERIVATIVE

(75) Inventor: Jutaro Syudo, Okawa-gun (JP)

(73) Assignee: Teikoku Seiyaku Co., Ltd., Kagawa (JP)

( * ) Notice: Subject to any disclaimer, the term of this patent is extended or adjusted under 35 U.S.C. 154(b) by 46 days.

(21) Appl. No.: 09/830,499

(22) PCT Filed: Aug. 11, 2000

(86) PCT No.: PCT/JP00/05423

§ 371 (c)(1),
(2), (4) Date: Apr. 25, 2001

(87) PCT Pub. No.: WO01/13915

PCT Pub. Date: Mar. 1, 2001

(30) Foreign Application Priority Data

Aug. 25, 1999 (JP) .......................................... 11-238910

(51) Int. Cl.⁷ ................................................ A61K 7/48
(52) U.S. Cl. .................... 424/402; 424/78.03; 424/401; 424/449; 424/684; 424/585; 424/690; 514/494; 514/944

(58) Field of Search ................................ 424/402, 401, 424/78.03, 449, 684, 685, 690; 514/474, 944

(56) References Cited

U.S. PATENT DOCUMENTS 6,432,431 B1 * 8/2002 Muta et al. ................ 424/402

FOREIGN PATENT DOCUMENTS

| GB | 2273044 | * | 6/1994 |
| JP | 2000-143484 | | 5/2000 |
| WO | WO-20000-2563 | * | 1/2001 |

* cited by examiner

*Primary Examiner*—Jyothsan Venkat
(74) *Attorney, Agent, or Firm*—Knobbe, Martens Olson & Bear LLP

(57) ABSTRACT

A cataplasm comprising crosslinked polymer gel containing vitamin C or a derivative thereof and a support, wherein the gel is formed by crosslinking a polymer with two kinds of substances selected from magnesium aluminometasilicate, dried aluminum hydroxide gel and aluminum chloride is prepared.

13 Claims, No Drawings

CATAPLASMS CONTAINING VITAMIN C OR ITS DERIVATIVE

This application is the U.S. National Phase under 35 U.S.C. § 371 of International Application PCT/JP00/05423, filed Aug. 11, 2000, which claims priority based on JP 11-238910, filed Aug. 25, 1999.

TECHNICAL FIELD

The present invention relates to a cataplasm containing vitamin C or a derivative thereof. More specifically, the present invention relates to a cataplasm comprising a crosslinked polymer gel containing vitamin C or a derivative thereof and a support.

BACKGROUND ART

Water-soluble adhesive ingredients are widely and routinely used today in conventional cataplasms such as antiphlogistic and analgetic cataplasms (plaster for external skin), moisture retention cosmetic pack and cooling gel sheets. They are formed by mixing kaolin or glycerin as a base with water-soluble polymer materials such as sodium polyacrylate or carboxymethylcellulose sodium, various active ingredients, water and so forth, and molding them, while its shape-retainability is secured by using a metal crosslinking agent.

DISCLOSURE OF THE INVENTION

Vitamin C or a derivative thereof has long been known to have an effect for preventing abnormal pigmentation by inhibiting skin melanin production, and it has been attempted to add vitamin C or a derivative thereof to cataplasms such as a cosmetic pack as an active ingredient for obtaining a skin-whitening effect. However, there is a problem that, when vitamin C or a derivative thereof is added to an adhesive cataplasm, a stable gel cannot be formed since water-soluble polymers are not crosslinked due to interaction of vitamin C or a derivative thereof and a metal crosslinking agent and thus the materials cannot be molded as a cataplasm.

As a result of efforts devoted to solve this problem, it was found that a gel-like cataplasm having favorable shape-retainability could be obtained by blending two kinds of substances selected from magnesium aluminometasilicate, dried aluminum hydroxide gel and aluminum chloride as crosslinking agents with a mixture of a water soluble polymer, glycerin, kaolin, water and so forth, and thus the present invention was accomplished.

That is, the present invention provides a cataplasm comprising crosslinked polymer gel containing vitamin C or a derivative thereof and a support, wherein the gel is formed by crosslinking a polymer with two kinds of substances selected from magnesium aluminometasilicate, dried aluminum hydroxide gel and aluminum chloride.

In the present invention, the polymer preferably consists of one or more kinds of materials selected from the group consisting of gelatin, gum arabic, glucomannan, xanthan gum, tragacanth gum, polyacrylic acid, sodium polyacrylate, polyvinyl alcohol, polyvinylpyrrolidone, carboxyvinyl polymer, carboxymethylcellulose sodium, hydroxypropylcellulose, methylcellulose, ethylcellulose, methyl vinyl ether/maleic anhydride copolymer, sodium polyalginate and polyethylene oxide.

In the present invention, the content of vitamin C or a derivative thereof is preferably 0.01–10 parts by weight per 100 parts by weight of the crosslinked polymer gel.

In the present invention, the sum of the contents of the two kinds of crosslinking agents selected from magnesium aluminometasilicate, dried aluminum hydroxide gel and aluminum chloride is preferably 0.5–5 parts by weight per 100 parts by weight of the crosslinked polymer gel.

In the present invention, the polymer content is preferably 1–40 parts by weight per 100 parts by weight of the crosslinked polymer gel.

Further, pH of the gel used for the cataplasm of the present invention is preferably in the range of 5.5–8.5. Moreover, the gel of the cataplasm of the present invention preferably further contains a polyhydric alcohol.

The cataplasm of the present invention containing vitamin C or a derivative thereof has excellent shape-retainability, since gel is formed by crosslinking of the polymer due to the inclusion of the two kinds of substances selected from magnesium aluminometasilicate, dried aluminum hydroxide gel and aluminum chloride.

Hereafter, the present invention will be explained in more detail.

The present invention provides a cataplasm comprising crosslinked polymer gel containing vitamin C or a derivative thereof and a support, wherein the gel is formed by crosslinking a polymer with two kinds of substances selected from magnesium aluminometasilicate, dried aluminum hydroxide gel and aluminum chloride. That is, the cataplasm of the present invention is characterized by containing vitamin C or a derivative thereof, two kinds of substances selected from magnesium aluminometasilicate, dried aluminum hydroxide gel and aluminum chloride and polymer. This cataplasm can provide various effects of vitamin C or a derivative thereof due to the inclusion of vitamin C or a derivative thereof as an active ingredient, and can show superior shape-retainability and adhesion since the polymer is crosslinked to form a gel even in the presence of vitamin C or a derivative thereof due to the inclusion of two kinds of substances selected from magnesium aluminometasilicate, dried aluminum hydroxide gel and aluminum chloride as crosslinking agents. Each of these ingredients will be explained below.

<1> Vitamin C or Derivative Thereof

The cataplasm of the present invention containing crosslinked polymer gel contains vitamin C, i.e., L-ascorbic acid, or a derivative of L-ascorbic acid. Examples of derivatives of L-ascorbic acid include various salts of L-ascorbic acid such as sodium L-ascorbate and L-ascorbyl magnesium phosphate, esters such as L-ascorbyl palmitate, L-ascorbyl stearate and isopropyl vitamin C and so forth. These vitamin C and derivatives thereof can be used each alone, or as a combination of two or more kinds of them. The amount thereof is preferably 0.01–10 parts by weight, more preferably 1–5 parts by weight, per 100 parts by weight of the crosslinked polymer gel. Since the cataplasm of the present invention contains vitamin C or a derivative thereof, there can be obtained various effects derived from vitamin C, for example, a skin-whitening effect obtained by inhibition of skin melanin production and so forth. As described above, the cataplasm of the present invention contains vitamin C or a derivative thereof as an active ingredient, but can also contain other active ingredients. Preferred examples of such active ingredients include sodium hyaluronate, vitamin A, collagen and so forth.

<2> Polymer Material

The cataplasm of the present invention contains a polymer. Examples of the polymer include natural polymers such as gelatin, gum arabic, glucomannan, xanthan gum and tragacanth gum, polyacrylic acid, sodium polyacrylate, polyvinyl alcohol, polyvinylpyrrolidone, carboxyvinyl polymer, cellulose derivatives such as carboxymethylcellulose sodium, hydroxypropylcellulose, methylcellulose and ethylcellulose, water-soluble synthetic polymers such as methyl vinyl ether/maleic anhydride copolymer, sodium polyalginate and polyethylene oxide and so forth. The molecular weight of these polymers is not particularly limited.

These polymers may be used each alone or as a combination of two or more kinds of them. Among these polymers, polyacrylic acid and sodium polyacrylate added with other polymers are preferably used. The amount of the polymer can be appropriately selected depending on the kind of polymer to be selected, but it is preferably 1–40 parts by weight, more preferably 5–20 parts by weight, per 100 parts by weight of the crosslinked polymer gel. A cataplasm having favorable shape-retainability and adhesion can be prepared by blending such an amount of the polymer.

<3> Crosslinking Agent

The cataplasm of the present invention containing crosslinked polymer gel contains two kinds of substances selected from magnesium aluminometasilicate, dried saluminum hydroxide gel and aluminum chloride as crosslinking agents.

The combination of magnesium aluminometasilicate, dried aluminum hydroxide gel and aluminum chloride for use in the present invention can be appropriately selected depending on the attaching site or desired adhesion of products. As magnesium aluminometasilicate, for example, Neusilin available from Fuji Chemical Industry Co., Ltd. can be used. As dried aluminum hydroxide gel, the dried aluminum hydroxide gel available from Kyowa Chemical Industry Co., Ltd. can be used. As aluminum chloride, aluminum chloride available from Wako Pure Chemical Industries, Ltd. can be used. Two kinds of substances can be appropriately selected from the above depending on the kind of polymer to be selected or required adhesion.

Chemical formulae of these crosslinking agents for use in the present invention are shown below. Magnesium aluminometasilicate: $Al_2O_3.MgO.2SiO_2.xH_2O$ Dried aluminum hydroxide gel: $Al_2O_3.nH_2O$ Aluminum chloride: $AlCl_3.6H_2O$ The amount of the two kinds of substances selected from magnesium aluminometasilicate, dried aluminum hydroxide gel, aluminum chloride is preferably 0.5–5 parts by weight, more preferably 0.7–3 parts by weight, per 100 parts by weight of the crosslinked polymer gel. The polymer can be crosslinked to form a gel by blending two kinds of substances selected from magnesium aluminometasilicate, dried aluminum hydroxide gel and aluminum chloride with the polymer in a proportion of 0.5–5 parts by weight even when vitamin C or a derivative thereof is contained, and thus a stable cataplasm which can maintain shape-retainability of the gel for a long period of time can be obtained.

When vitamin C or a derivative thereof is added to such a cataplasm, the polymer is not usually crosslinked due to interaction between vitamin C or a derivative thereof and the crosslinking agent. However, the polymer is favorably crosslinked by using the two kinds of substances selected from magnesium aluminometasilicate, dried aluminum hydroxide gel and aluminum chloride as crosslinking agents.

<4> Cataplasm

The cataplasm of the present invention comprising the crosslinked polymer gel contains an appropriate amount of water in addition to the aforementioned ingredients. The content of water is preferably 20–80 parts by weight, more preferably 30–60 parts by weight, per 100 parts by weight of the crosslinked polymer gel.

The cataplasm preferably further contains a polyhydric alcohol such as glycerin, sorbitol, propylene glycol, 1,3-butylene glycol or ethylene glycol among various additives for use in usual cataplasms. Among these polyhydric alcohols, glycerin, sorbitol or propylene glycol is preferably used. The content of polyhydric alcohol is preferably 5–40 parts by weight, more preferably 10–30 parts by weight, per 100 parts by weight of the crosslinked polymer gel. By blending these polyhydric alcohols in an amount within an appropriate range, shape-retainability and adhesion can be stably maintained for a long period of time.

Further, the cataplasm of the present invention preferably contains an inorganic substance such as kaolin, bentonite or titanium oxide. Kaolin is preferably used among these inorganic substances. The content of the inorganic substance is preferably 0.1–20 parts by weight, more preferably 2–10 parts by weight, per 100 parts by weight of the crosslinked polymer gel. By blending these inorganic substances, cohesion of the cataplasm or plaster can be improved.

The cataplasm of the present invention may optionally contain various additives for use in usual cataplasms as required. Examples of such additives include, for example, alcohols such as ethanol and isopropanol, antioxidants such as sodium hydrogensulfite and erythorbic acid, preservatives such as methylparaben and propylparaben, surfactants such as hydrogenated caster oil, oils such as hohoba oil or eucalyptus oil, chelating agents such as sodium edetate, pH regulators such as sodium hydroxide or tartaric acid, perfumes, coloring matters and so forth. The kinds of these additives are not particularly limited, and those conventionally used in cataplasms, packs, ointments, gels, creams and so forth can be appropriately selected and used. The contents thereof are not also particularly limited, and can be adjusted depending on the purpose.

Further, pH of the cataplasm of the present invention is preferably in the range of 5.5–8.5, more preferably 6.0–8.0. When the cataplasm is used in the range of pH 5.5–8.5, it shows favorable shape-retainability, adhesion and stability for long-term storage. The pH of the cataplasm can be measured by using a usual pH meter, for example.

The cataplasm of the present invention is used as a cataplasm comprising a support as described below from viewpoints of ease of use and obtaining continuous effects of vitamin C or a derivative thereof or other active ingredients.

A cataplasm comprising a support can be prepared, for example, as described below. That is, a plaster (gel) is prepared as a paste by uniformly mixing the aforementioned respective ingredients, coated and spread on a support such as paper, non-woven fabric or plastic film in a conventional manner to obtain a cataplasm. To protect the cataplasm, a release paper sheet may be stuck on the surface thereof, and the cataplasm may be cut into a predetermined size for use. The method of preparing the cataplasm is not particularly limited, and methods usually used for the preparation of cataplasms can be appropriately used.

As the support, paper, non-woven fabric, plastic film or the like can be used and is not particularly limited. However, non-woven fabric or knit is preferably used.

By using two kinds of substances selected from magnesium aluminometasilicate, dried aluminum hydroxide gel and aluminum chloride as crosslinking agents for a paste containing vitamin C or a derivative thereof, water-soluble polymer and water in the cataplasm of the present invention, the polymer can be crosslinked to form a stable gel. It was found that this cataplasm was hardly solidified, did not cause separation due to dehydration, exudation from back face of the support, overflow from the periphery of the support and so forth, and had stable shape-retainability.

BEST MODE FOR CARRYING OUT THE INVENTION

Hereafter, the present invention will be explained in detail with reference the following examples. However, the present invention should not be limited by the following examples. EXAMPLES 1–6

Ingredients listed in Table 1 mentioned below were mixed to obtain various plasters (gel). Each of the obtained plasters was spread on base fabric composed of polyester fibers in an amount of 1000 g/m², and a release paper sheet was stuck on the plaster surface to obtain a cataplasm.

TABLE 1

| Ingredient | Example 1 | 2 | 3 | 4 | 5 | 6 |
|---|---|---|---|---|---|---|
| Magnesium alumino-metasilicate | 1 | 3 | — | — | 1 | 3 |
| Dried aluminum hydroxide gel | — | — | 1 | 3 | 3 | 1 |
| Aluminum chloride | 3 | 1 | 3 | 1 | — | — |
| L-Ascorbic acid | 3 | 3 | 3 | — | — | — |
| L-Ascorbyl magnesium phosphate | — | — | — | 3 | 3 | 3 |
| D-Sorbitol | 20 | 5 | — | 8 | — | 15 |
| Glycerin | 18 | 20 | 15 | — | 9 | — |
| Propylene glycol | — | — | 5 | 15 | 10 | 5 |
| Polyethylene glycol | — | — | — | — | 7 | 13 |
| Kaolin | 3 | — | 2 | — | — | — |
| Tartaric acid | — | — | 0.4 | — | 0.1 | — |
| Malic acid | 0.5 | — | — | — | 0.4 | — |
| Triethanolamine | — | 1 | — | 0.5 | — | 0.3 |
| Sodium hydroxide | — | 0.2 | — | — | — | — |
| Methylparaben | 1 | 1 | 1 | 1 | 1 | 1 |
| Propylparaben | 0.5 | 0.5 | 0.5 | 0.5 | 0.5 | 0.5 |
| Polyacrylic acid | 4 | — | 2 | — | 3 | — |
| Sodium polyacrylate | 4 | 5 | — | 7 | 4 | 6 |
| Polyvinylpyrrolidone | 1 | — | 3 | — | — | — |
| Carboxymethylcellulose sodium | — | 5 | 5 | 3 | — | 5 |
| Sodium alginate | 4 | — | — | — | 6 | — |
| EDTA | 0.05 | 0.03 | 0.02 | 0.02 | 0.01 | 0.01 |
| Purified water | 36.95 | 55.27 | 59.08 | 57.98 | 51.99 | 47.19 |
| Total | 100 | 100 | 100 | 100 | 100 | 100 |
| PH | 5.5 | 8.5 | 6.0 | 7.5 | 6.5 | 7.0 |

Comparative Examples 1–3

Cataplasms of Comparative Examples 1–3 were prepared by using the ingredients used in Examples 1–3 except that the magnesium aluminometasilicate, dried aluminum hydroxide gel and aluminum chloride were replaced with the same amount of alumina magnesium hydroxide.

Comparative Examples 4–6

Cataplasms of Comparative Examples 4–6 were prepared by using the ingredients used in Examples 1–3 except that the magnesium aluminometasilicate, dried aluminum hydroxide gel and aluminum chloride were replaced with the same amount of synthetic hydrotalcite.

Comparative Examples 7–9

Cataplasms of Comparative Examples 7–9 were prepared by using the ingredients used in Examples 1–3 except that the magnesium aluminometasilicate, dried aluminum hydroxide gel and aluminum chloride were replaced with the same amount of dihydroxyaluminum aminoacetate.

Comparative Examples 10–12

Cataplasms of Comparative Examples 10–12 were prepared by using the ingredients used in Examples 4–6 except that the magnesium aluminometasilicate, dried aluminum hydroxide gel and aluminum chloride were replaced with the same amount of aluminum hydroxide.

<Evaluation of Cataplasms>

The cataplasms prepared in the examples and comparative examples were evaluated as follows. That is, each of the cataplasms of Examples 1–6 and Comparative Example 1–12 was placed in a bag, sealed and stored in a thermo-hygrostat adjusted to room temperature, i.e., 40±2° C., and 75% of relative humidity (RH) for 2 weeks. Subsequently, each cataplasm in the bag was taken out from the thermo-hygrostat and returned to room temperature. The bag was opened and then each cataplasm was evaluated. That is, overflow of plaster, exudation from back face of non-woven fabric, adhesion of plaster to a polyethylene film upon removal of the film, adhesion of plaster to human skin after applied to and removed from the skin were evaluated by organoleptic examination according to the criteria shown in Table 2 mentioned below. The results are shown in Table 3 mentioned below. The adhesion of plaster to human skin after applied to and removed from the skin was evaluated by applying each cataplasm on the skin and then removing the cataplasm from the skin 2 hours later.

TABLE 2

| Evaluation criteria | |
|---|---|
| − | Not observed at all |
| ± | Slightly observed |
| + | Significantly observed |

TABLE 3

| | Overflow of plaster | Exudation from back face of non-woven fabric | Adhesion of plaster to film | Adhesion of plaster to human skin |
|---|---|---|---|---|
| Example 1 | − | − | − | − |
| Example 2 | − | − | − | − |
| Example 3 | − | − | − | − |
| Example 4 | − | − | − | − |
| Example 5 | − | − | − | − |
| Example 6 | − | − | − | − |
| Comparative Example 1 | + | + | + | + |
| Comparative Example 2 | + | + | + | + |
| Comparative Example 3 | + | ± | + | + |
| Comparative Example 4 | ± | + | ± | + |
| Comparative Example 5 | + | + | ± | ± |

TABLE 3-continued

| | Overflow of plaster | Exudation from back face of nonwoven fabric | Adhesion of plaster to film | Adhesion of plaster to human skin |
|---|---|---|---|---|
| Comparative Example 6 | + | + | + | + |
| Comparative Example 7 | + | ± | + | + |
| Comparative Example 8 | + | + | + | ± |
| Comparative Example 9 | + | ± | + | + |
| Comparative Example 10 | ± | + | ± | + |
| Comparative Example 11 | + | + | + | + |
| Comparative Example 12 | + | + | + | ± |

As clearly seen from the results shown in the above Table 3, the cataplasms of the present invention exhibited superior shape-retainability as cataplasms without showing overflow of plaster, exudation from back face and adhesion of plaster. The cataplasms of Examples 1–3 similarly did not show any overflow of plaster, exudation from back face or adhesion of plaster even after they were stored at 40° C. for 1, 3 or 6 months according to the above test method.

Industrial Applicability

The cataplasm of the present invention containing vitamin C or a derivative thereof shows superior shape-retainability since the polymer is crosslinked with magnesium aluminometasilicate and so forth to form a gel.

What is claimed is:

1. A cataplasm comprising:
   a crosslinked polymer gel wherein a polymer is crosslinked with at least two types of substances selected from the group consisting of magnesium aluminometasilicate, dried aluminum hydroxide gel, and aluminum chloride;
   vitamin C or its derivative which is incorporated in the crosslinked polymer gel; and
   a support on which the crosslinked polymer gel is applied.

2. The cataplasm according to claim 1, wherein the polymer is one or more kinds of materials selected from the group consisting of gelatin, gum arabic, glucomannan, xanthan gum, tragacanth gum, polyacrylic acid, sodium polyacrylate, polyvinyl alcohol, polyvinylpyrrolidone, carboxyvinyl polymer, carboxymethylcellulose sodium, hydroxypropylcellulose, methylcellulose, ethylcellulose, methyl vinyl ether/maleic anhydride copolymer, sodium polyalginate and polyethylene oxide.

3. The cataplasm according to claim 1, wherein the vitamin C or its derivative is contained in an amount of 0.01–10 parts by weight per 100 parts by weight of the crosslinked polymer gel.

4. The cataplasm according to claim 1, wherein the at least two types of substances are contained in an amount of 0.5–5 parts by weight per 100 parts by weight of the crosslinked polymer gel.

5. The cataplasm according to claim 1, wherein the polymer is contained in an amount of 1–40 parts by weight per 100 parts by weight of the crosslinked polymer gel.

6. The cataplasm according to claim 1, wherein the pH of the crosslinked polymer gel is in the rage of approximately 5.5–8.5.

7. The cataplasm according to claim 1, further comprising polyhydric alcohol.

8. A method for preparing a cataplasm, comprising:
   preparing a polymer material comprising a polymer and vitamin C or its derivative;
   crosslinking the polymer material to obtain a crosslinked polymer gel by adding at least two types of substances selected from the group consisting of magnesium aluminometasilicate, dried aluminum hydroxide gel, and aluminum chloride; and
   applying the crosslinked polymer gel on a support.

9. The method according to claim 8, wherein the vitamin C or its derivative is used in an amount of 0.01–10 parts by weight per 100 parts by weight of the crosslinked polymer gel.

10. The method according to claim 8, wherein the at least two types of substances are added in an amount of 0.5–5 parts by weight per 100 parts by weight of the crosslinked polymer gel.

11. The method according to claim 8, wherein the polymer is used in an amount of 1–40 parts by weight per 100 parts by weight of the crosslinked polymer gel.

12. The method according to claim 8, wherein the pH of the crosslinked polymer gel is adjusted in the rage of approximately 5.5–8.5.

13. The method according to claim 8, further comprising adding polyhydric alcohol to the polymer material.

* * * * *